United States Patent
Ci

(10) Patent No.: US 10,433,575 B2
(45) Date of Patent: Oct. 8, 2019

(54) NUTRITIONAL COMPOSITION FOR TONIFYING KIDNEY AND METHOD FOR PREPARING THE SAME

(71) Applicant: Zhonghua Ci, Beijing (CN)

(72) Inventor: Zhonghua Ci, Beijing (CN)

( * ) Notice: Subject to any disclaimer, the term of this patent is extended or adjusted under 35 U.S.C. 154(b) by 0 days.

(21) Appl. No.: 15/934,715

(22) Filed: Mar. 23, 2018

(65) Prior Publication Data

US 2019/0159490 A1    May 30, 2019

(30) Foreign Application Priority Data

Nov. 30, 2017   (CN) .......................... 2017 1 1244237

(51) Int. Cl.
| | |
|---|---|
| *A23L 7/196* | (2016.01) |
| *A23L 19/10* | (2016.01) |
| *A23L 25/00* | (2016.01) |
| *A23L 5/10* | (2016.01) |
| *A61K 36/8945* | (2006.01) |
| *A61K 36/815* | (2006.01) |
| *A61K 36/076* | (2006.01) |

(52) U.S. Cl.
CPC .............. *A23L 7/1965* (2016.08); *A23L 5/10* (2016.08); *A23L 19/10* (2016.08); *A23L 25/20* (2016.08); *A61K 36/076* (2013.01); *A61K 36/815* (2013.01); *A61K 36/8945* (2013.01); *A23V 2002/00* (2013.01); *A23V 2200/30* (2013.01); *A23V 2250/208* (2013.01); *A23V 2250/21* (2013.01); *A23V 2300/10* (2013.01); *A23V 2300/16* (2013.01); *A23V 2300/48* (2013.01)

(58) Field of Classification Search
None
See application file for complete search history.

(56) References Cited

U.S. PATENT DOCUMENTS

2015/0296851 A1* 10/2015 Zhao .......................... A23F 3/34
426/2

FOREIGN PATENT DOCUMENTS

| CN | 105962051 A | * | 9/2016 |
|---|---|---|---|
| CN | 107343935 A | * | 11/2017 |

* cited by examiner

*Primary Examiner* — Robert A Wax
*Assistant Examiner* — Melissa S Mercier
(74) *Attorney, Agent, or Firm* — Cantor Colburn LLP

(57) ABSTRACT

The present application discloses a nutritional composition for tonifying kidney. The nutritional composition comprises the following components of raw materials in parts by weight: rice 50-90, yellow millet 7-25, gordon euryale seed 3-14, Chinese yam 2-11, *lycium barbarum* 0.4-1.6, and poria 0.3-1.5. The present invention, in view of the kidney's main function of reserving and storing the essence of internal organs of the body, complies with the functional characteristics that it is appropriate to reserve rather than consume the kidney, and provides the prescription for more nourishment and less loss and suitable to cooperate with staple foods for long-term consumption, and it is easily accepted by people due to the good taste, and can achieve certain efficacies of tonifying the kidney and disinhibiting the body.

9 Claims, 1 Drawing Sheet

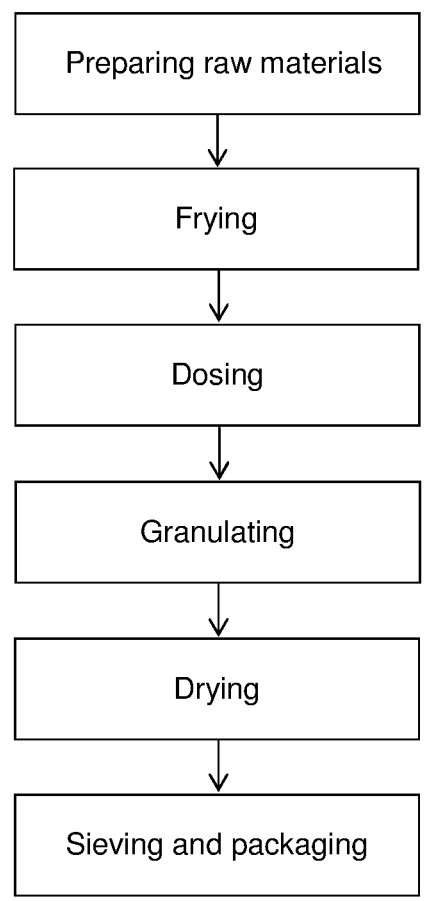

NUTRITIONAL COMPOSITION FOR TONIFYING KIDNEY AND METHOD FOR PREPARING THE SAME

TECHNICAL FIELD

The present invention belongs to the technical field of food processing, and particularly relates to a nutritional composition for tonifying kidney and a method for preparing the same.

BACKGROUND

Fast-pace and High-intensity work, deliberate competition, ceaseless stress, long-term metal strain and so on are heavy burdens for people in modern society. Moreover, when reaching middle ages, people's physiological functions decline, and many people develop syndromes belonging to kidney deficiency in traditional Chinese medical science, such as pains in waist and back, tinnitus, dizziness, pale facial complexion, declined physical functions, cold extremities, mental fatigue, and sleeping disorder, all of which further form invisible metal stress, and seriously affect the life quality. Traditional Chinese medical science holds that the kidney is "the congenital foundation", "the root of life", and "the pivot of vitality". It has the physiological functions of storing essence, governing water, qi absorption, and bones, and producing marrow, and is mainly related to skeletal development, blood circulation, skin, and even teeth and ears of the human body. In a word, the functions and health condition of the kidney can reflect booms and busts and vitality of the growth, evolution, and reproductive system of the human body. In the traditional medicines of more than 5000 years of the Chinese nation, some natural plant drugs indeed have curative effects in repairing and improving the kidney functions. The invaluable experience, handed down from generation to generation, upon continuous application, development, and perfection of medical experts and health experts of successive dynasties, has become a type of unique natural plant drug (Chinese herbal medicine for tonifying the kidney) with the nourishing and strengthening efficacies. However, every medicine has its side effect, and long-term consumption of a lot of Chinese herbal medicine inevitably will cause damages to other aspects of the body.

On the basis of dietotherapy (homology between medicine and food) regimen of the traditional Chinese medical science, more and more dieticians reasonably match food materials with the homology between medicine and food, and achieve the object of nourishing yin and tonifying the kidney through the function of channel tropism of the food materials' four natures and five tastes.

Currently, similar health-care products with the function of tonifying the kidney are already available in the market, but in most cases, the matching of different foods is chaotic, does not follow the pharmacology, and has relatively bad taste.

DISCLOSURE OF THE INVENTION

A main object of the present invention is to provide a health-care food for tonifying kidney and disinhibiting the body.

In order to achieve the above object, according to one aspect of the present invention, a nutritional composition for tonifying kidney is provided.

The nutritional composition for tonifying kidney according to the present invention includes the following components of raw materials in parts by weight: rice 50-90, yellow millet 7-25, gordon euryale seed 3-14, Chinese yam 2-11, *lycium barbarum* 0.4-1.6, and poria 0.3-1.5.

Furthermore, the nutritional composition for tonifying kidney includes the following components of raw materials in parts by weight: rice 60-80, yellow millet 10-20, gordon euryale seed 5-9, Chinese yam 4-8, *lycium barbarum* 0.7-1.3, and poria 0.6-1.2.

Furthermore, the nutritional composition for tonifying kidney includes the following components of raw materials in parts by weight: rice 70, yellow millet 15, gordon euryale seed 7, Chinese yam 6, *lycium barbarum* 1, and poria 1.

Furthermore, the nutritional composition for tonifying kidney further includes a Chinese herbal medicine extract of 1-3 parts, wherein the Chinese herbal medicine extract includes the following components of raw materials in parts by weight: perilla 15-30, raspberry 17-28, cinnamon 16-28, fennel 10-20, and ginger 16-23.

In order to achieve the above object, according to another aspect of the present invention, a method for processing a nutritional composition for tonifying kidney is further provided.

The method for processing a nutritional composition for tonifying kidney according to the present invention includes the following steps in sequence:

step 1, preparing raw materials: purifying and sorting rice, yellow millet, gordon euryale seed, Chinese yam, *lycium barbarum*, and poria for subsequent use;

step 2, frying: frying respective components of raw materials under a condition of 100-200° C. for 25-120 min;

step 3, dosing: grinding the respective fried raw materials, then mixing and stirring evenly the respective ground raw materials according to proportions to obtain a rice powder;

step 4, granulating: extruding the rice powder obtained in step 3 through a double-screw extruder, followed by gelatinization and granulation, to obtain mixed rice grains;

step 5, drying: drying the mixed rice grains through a microwave dryer, wherein a water content of the material is kept below 12%, and cooling the dried mixed rice grains at a room temperature;

step 6, sieving and packaging: sieving the cooled mixed rice grains, and vacuum-packaging the sieved mixed rice grains.

Furthermore, temperatures of three phases of the double-screw extruder are kept at 60° C., 90-120° C., and 90° C., respectively.

Furthermore, a heating temperature of the microwave dryer is kept at 50-60° C.

Furthermore, in a dosing process of the step 3, a Chinese herbal medicine extract of 1-3 parts is further added, and the Chinese herbal medicine extract includes the following components of raw materials in parts by weight: perilla 15-30, raspberry 17-28, cinnamon 16-28, fennel 10-20, and ginger 16-23.

Furthermore, the Chinese herbal medicine extract is prepared through the following method:

drying and grinding respective raw materials into a medicinal powder, subjecting the medicinal powder to ultrasonic extraction, centrifugation, and concentration with an ethanol solution of 40-65% in volume percentage to obtain the Chinese herbal medicine extract.

Furthermore, in a process of preparing the Chinese herbal medicine extract, a vacuum dryer is used for drying, a temperature parameter is 75° C.-80° C., and a vacuum degree is between a negative pressure of 0.08 MPa and a negative pressure of 0.1 MPa.

The present invention, in view of the kidney's main function of reserving and storing the essence of internal organs of the body, complies with the functional characteristics that it is appropriate to reserve rather than consume the kidney, and provides the prescription for more nourishment and less loss and suitable to cooperate with staple foods for long-term consumption, and it is easily accepted by people due to the good taste, and can achieve certain efficacies of tonifying the kidney and disinhibiting the body.

BRIEF DESCRIPTION OF DRAWINGS

The FIGURE, constituting a portion of the present application, is used for further understanding of the present invention, so as to make it more obvious other features, objects, and advantages of the present application. Exemplary examples of the present invention, drawings, and description thereof are used to explain the present invention, rather than improperly limiting the present invention. In the FIGURE, FIG. 1 is a flow chart of a technology for processing a nutritional composition of examples of the present invention.

DETAILED DESCRIPTION OF EMBODIMENTS

In order to make a person skilled in the art better understand solutions of the present application, below technical solutions of the examples of the present application will be described clearly and completely in conjunction with the FIGURE of the examples of the present application. Apparently, some but not all of examples of the present application are described. Based on the examples of the present application, all the other examples, which a person ordinarily skilled in the art obtains without paying inventive effort, fall within the scope of protection of the present application.

Besides, the term "include (comprise)" and any variants thereof are intended to cover non-exclusive containing, for example, a product including a series of raw materials or a method including a series of steps is not necessarily limited to listing those raw materials or steps, but may include other steps or raw materials which are not clearly listed or inherent to the method or product.

It should be indicated that examples of the present application and features in the examples can be combined with each other without conflict. The present application will be described in detail with reference to the FIGURES in conjunction with the examples.

A main object of the present invention is to provide a health-care food for tonifying kidney and disinhibiting the body.

In one aspect, the present invention provides a nutritional composition for tonifying kidney having such function, including the following components of raw materials in parts by weight: rice 50-90, yellow millet 7-25, gordon euryale seed 3-14, Chinese yam 2-11, lycium barbarum 0.4-1.6, and poria 0.3-1.5.

Rice: the traditional Chinese medical science holds that rice is sweet in taste and mild in nature, exerts the curative effect through the spleen, stomach, and lung channels, has the efficacy of nourishing the middle energizer and supplementing qi (vital energy), tonifying the spleen and nourishing the stomach, replenishing the essence and improving the memory, harmonizing the internal organs, promoting the blood circulation, improving the hearing and eyesight, eliminating annoyance, quenching thirst, and curing diarrhea, and it is considered that taking more rice can "strengthen the body and improve the look".

Yellow millet: yellow millet, slightly cold in nature and sweet in taste, exerts the curative effect through the lung, stomach, and large intestine channels, supplements yin, disinhibits the lungs and large intestine, and is used for treatment of yang excess and yineficiency, sleepless at night, chromatic-diarrhea dyspepsia, chilblain, scabies, toxic-heat, and toxic mass.

Gordon euryale seed: gordon euryale seed, sweet and astringent in taste, and mild in nature, exerts the curative effect through the spleen and kidney channels, invigorates kidney to strengthen essence, nourishes spleen, cures diarrhea, dispels dampness, arrests leucorrhoea, and is used for treatment of gonobolia and spermatorrhea, enuresis and frequent urination, lung-deficiency chronic diarrhea, gonorrhea, and leucorrhoea.

Chinese yam: Chinese yam, sweet in taste and mild in nature, exerts the curative effect through the spleen, lung, and kidney channels, supplements qi, nourishes yin, tonifies the spleen and lung, tonifyes kidney to strengthen essence, and is used for treatment of reduced spleen-deficiency appetite, loose stool with indigested grains, lung-deficiency cough, gonobolia, frequent urination, and yin-deficiency diabetes.

*Lycium barbarum: lycium barbarum*, mild in nature and sweet in taste, exerts the curative effect through the liver and kidney channels, nourishes the liver and kidney, strengthens essence, improves eyesight, and is used for treatment of consumptive deficiency of spermatozoa, pains in waist and knee, dizziness and tinnitus, internal heat diabetes, sallow complexion due to blood deficiency, and blurred vision.

Poria: poria, sweet and light in taste, and mild in nature, exerts the curative effect through the heart, lung, spleen, and kidney channels, moistens dryness and promotes diuresis, tonifies the spleen, calms the heart, and is used for treatment of edema and oliguria, phlegm-fluid retention, reduced spleen-deficiency appetite, loose stool diarrhea, unease, and palpitation and insomnia.

The nutritional composition for tonifying kidney of the present invention achieves a perfect combination of dietotherapy and medical therapy by scientifically matching the principle of medicinal and edible dual purposes in combination with reasonable traditional Chinese medicines, reflecting the traditional preparing characteristics of the Chinese herbal medicine and providing the prescription based on the theory of the traditional Chinese medical science, and further enriching the purposes of the nutritional composition for tonifying kidney, i.e. regulation, balancing, supplementation, and keeping fit. It has the main efficacy of tonifying yang and kidney and supporting the healthy energy. The above composition can be taken as daily regulation diet.

On the basis of the above examples, the nutritional composition for tonifying kidney further includes a Chinese herbal medicine extract of 1-3 parts, wherein the Chinese herbal medicine extract includes the following components of raw materials in parts by weight: *perilla* 15-30, raspberry 17-28, cinnamon 16-28, fennel 10-20, and ginger 16-23.

*Perilla: perilla*, acrid in taste and warm in nature, exerts the curative effect through the lung and spleen channels, relieves exterior syndrome by diaphoresis, regulates qi and the middle energizer, and detoxifies ciguatoxin and crab poison, and is used for treatment of common cold due to wind-cold, headache, cough, thoracico-abdominal distention, and fish and crab poisoning.

Raspberry: raspberry, sweet and sour in taste, and warm in nature, exerts the curative effect through the liver, kidney, and urinary bladder channels, invigorates kidney to strengthen essence and reduce urination, and nourishes the liver to improve eyesight, and is used for treatment of gonobolia and spermatorrhea, enuresis and frequent urination, impotence and premature ejaculation, and blurring and dim vision.

Cinnamon: cinnamon, acrid and sweet in taste and extremely hot in nature, exerts the curative effect through the kidney, spleen, heart, and liver channels, has the efficacy of tonifying fire and helping yang, guiding fire to origin, eliminating cold to stop pain, and warming the meridians, and is used for treatment of impotence and uterine cold, waist and knee crymodynia, kidney deficiency asthma, yang deficiency with upper manifestation, dizziness and hot eyes, heart and abdomen crymodynia, deficiency-cold vomiting and diarrhea, cold abdominal colic stomachache, dysmenorrhea and amenorrhea.

Fennel: fennel, acrid in taste and warm in nature, exerts the curative effect through the liver, kidney, bladder, and stomach channels, warms the kidney and liver, promotes the circulation of qi to relieve pains, and harmonizes stomach, and is mainly used for treatment of cold abdominal colic stomachache, testicle sagging, abdominal fullness crymodynia, reduced appetite and vomiting, hypochondriac pain, kidney-deficiency lumbago, and dysmenorrhea.

Ginger: ginger, acrid in taste and hot in nature, exerts the curative effect through the spleen, stomach, kidney, heart, and lung channels, warms the middle energizer for dispelling cold, restores yang and promotes coronary circulation, warms the lungs, and resolves fluid, and is used for the treatment of abdominal fullness crymodynia, vomit, diarrhea, cold limbs, faint pulse, cold fluid, cough and asthma.

A small amount of the Chinese herbal medicine extract is added to the nutritional composition for improving the kidney tonifying function of the nutritional composition. In the Chinese herbal medicine extract, fennel and ginger are used for warming the kidney and liver, and warming the middle energizer and dispelling cold; cinnamon is used for warmly tonifying kidney-yang; *perilla* can dispel cold, promote the circulation of qi, and regulate the middle energizer; raspberry can achieve the purpose of invigorating the kidney and astringing the essences. The kidney-deficiency symptoms can be improved by combining various drugs. Moreover, the usage amount of the Chinese herbal medicine extract is relatively small, then it will not destroy the nutritional structure of the original nutritional composition for tonifying kidney, and will not produce an undesirable taste.

As shown in FIG. 1, a method for preparing the nutritional composition for tonifying kidney includes the following steps in sequence:

step 1, preparing raw materials: purifying and sorting rice, yellow millet, gordon euryale seed, Chinese yam, *lycium barbarum*, and poria for subsequent use, wherein the raw materials are strictly checked, and impurities and soils are removed, effectively reducing the remnant of pollutants such as heavy metals and pesticides;

step 2, frying: frying respective components of raw materials under a condition of 100-200° C. for 25-120 min, wherein the temperature should not be too high to make the starchy food produce acrylamide, thus preventing loss of nutrients;

step 3, dosing: grinding the respective fried raw materials, then mixing and stirring evenly the respective ground raw materials according to proportions to obtain a rice powder, wherein the proportions of the respective raw materials are based on the prescription of the nutritional composition for tonifying kidney of the present invention, and in the dosing process, a Chinese herbal medicine extract of 1-3 parts is further added, and the Chinese herbal medicine extract includes the following components of raw materials in parts by weight: *perilla* 15-30, raspberry 17-28, cinnamon 16-28, fennel 10-20, and ginger 16-23. Specifically, the Chinese herbal medicine extract can be prepared through the following method: drying and grinding respective raw materials into a medicinal powder, subjecting the medicinal powder to ultrasonic extraction, centrifugation, and concentration with an ethanol solution of 40-65% in volume percentage to obtain the Chinese herbal medicine extract. In a process of preparing the Chinese herbal medicine extract, a vacuum dryer is used for drying, a temperature parameter is 75° C.-80° C., and a vacuum degree is between a negative pressure of 0.08 MPa and a negative pressure of 0.1 MPa;

step 4, granulating: extruding the rice powder obtained in step 3 through a double-screw extruder, followed by gelatinization and granulation, to obtain mixed rice grains, wherein temperatures of three phases of the double-screw extruder are kept at 60° C., 90-120° C., and 90° C., respectively;

step 5: drying: drying the mixed rice grains through a microwave dryer, wherein a water content of the material is kept below 12%, and cooling the dried mixed rice grains at a room temperature, wherein a heating temperature of the microwave dryer is kept at 50-60° C.;

step 6: sieving and packaging: sieving the cooled mixed rice grains, and vacuum-packaging the sieved mixed rice grains, wherein the appearance and homogeneity of product particles can be improved by sieving, and in practical operation, after completing the packaging, a product name, a product lot number, specification, net weight, date of manufacture, name of position, and person in charge are recorded and tagged, and a delivery receipt is filled in, then the product is transferred to an intermediate station.

Example 1

A nutritional composition for tonifying kidney includes the following components of raw materials in parts by weight: rice 50, yellow millet 7, gordon euryale seed 3, Chinese yam 2, *lycium barbarum* 0.4, and poria 0.3.

A preparation method is as follows:

step 1, preparing raw materials: purifying and sorting rice, yellow millet, gordon euryale seed, Chinese yam, *lycium barbarum*, and poria for subsequent use;

step 2, frying: frying respective components of raw materials under a condition of 100° C. for 120 min;

step 3, dosing: grinding the respective fried raw materials, then mixing and stirring evenly the respective ground raw materials according to proportions to obtain a rice powder;

step 4, granulating: extruding the rice powder obtained in step 3 through a double-screw extruder, followed by gelatinization and granulation, to obtain mixed rice grains, wherein temperatures of three phases of the double-screw extruder are kept at 60° C., 90° C., and 90° C., respectively;

step 5: drying: drying the mixed rice grains through a microwave dryer, wherein a water content of the material is kept below 12%, and cooling the dried mixed rice grains at a room temperature, wherein a heating temperature of the microwave dryer is kept at 50° C.;

step 6: sieving and packaging: sieving the cooled mixed rice grains, and vacuum-packaging the sieved mixed rice grains.

Example 2

A nutritional composition for tonifying kidney includes the following components of raw materials in parts by weight: rice 90, yellow millet 25, gordon euryale seed 14, Chinese yam 11, *lycium barbarum* 1.6, and poria 1.5.

A preparation method is as follows:

step 1, preparing raw materials: purifying and sorting rice, yellow millet, gordon euryale seed, Chinese yam, *lycium barbarum*, and poria for subsequent use;

step 2, frying: frying respective components of raw materials under a condition of 200° C. for 25 min;

step 3, dosing: grinding the respective fried raw materials, then mixing and stirring evenly the respective ground raw materials according to proportions to obtain a rice powder;

step 4, granulating: extruding the rice powder obtained in step 3 through a double-screw extruder, followed by gelatinization and granulation, to obtain mixed rice grains, wherein temperatures of three phases of the double-screw extruder are kept at 60° C., 120° C., and 90° C., respectively;

step 5: drying: drying the mixed rice grains through a microwave dryer, wherein a water content of the material is kept below 12%, and cooling the dried mixed rice grains at a room temperature, wherein a heating temperature of the microwave dryer is kept at 60° C.;

step 6: sieving and packaging: sieving the cooled mixed rice grains, and vacuum-packaging the sieved mixed rice grains.

Example 3

A nutritional composition for tonifying kidney includes the following components of raw materials in parts by weight: rice 60, yellow millet 10, gordon euryale seed 5, Chinese yam 4, *lycium barbarum* 0.7, and poria 0.6.

A preparation method is as follows:

step 1, preparing raw materials: purifying and sorting rice, yellow millet, gordon euryale seed, Chinese yam, *lycium barbarum*, and poria for subsequent use;

step 2, frying: frying respective components of raw materials under a condition of 120° C. for 80 min;

step 3, dosing: grinding the respective fried raw materials, then mixing and stirring evenly the respective ground raw materials according to proportions to obtain a rice powder;

step 4, granulating: extruding the rice powder obtained in step 3 through a double-screw extruder, followed by gelatinization and granulation, to obtain mixed rice grains, wherein temperatures of three phases of the double-screw extruder are kept at 60° C., 100° C., and 90° C., respectively;

step 5: drying: drying the mixed rice grains through a microwave dryer, wherein a water content of the material is kept below 12%, and cooling the dried mixed rice grains at a room temperature, wherein a heating temperature of the microwave dryer is kept at 58° C.;

step 6: sieving and packaging: sieving the cooled mixed rice grains, and vacuum-packaging the sieved mixed rice grains.

Example 4

A nutritional composition for tonifying kidney includes the following components of raw materials in parts by weight: rice 80, yellow millet 20, gordon euryale seed 9, Chinese yam 8, *lycium barbarum* 1.3, and poria 1.2.

A preparation method is as follows:

step 1, preparing raw materials: purifying and sorting rice, yellow millet, gordon euryale seed, Chinese yam, *lycium barbarum*, and poria for subsequent use;

step 2, frying: frying respective components of raw materials under a condition of 130° C. for 60 min;

step 3, dosing: grinding the respective fried raw materials, then mixing and stirring evenly the respective ground raw materials according to proportions to obtain a rice powder;

step 4, granulating: extruding the rice powder obtained in step 3 through a double-screw extruder, followed by gelatinization and granulation, to obtain mixed rice grains, wherein temperatures of three phases of the double-screw extruder are kept at 60° C., 105° C., and 90° C., respectively;

step 5: drying: drying the mixed rice grains through a microwave dryer, wherein a water content of the material is kept below 12%, cooling the dried mixed rice grains at a room temperature, wherein a heating temperature of the microwave dryer is kept at 53° C.;

step 6: sieving and packaging: sieving the cooled mixed rice grains, and vacuum-packaging the sieved mixed rice grains.

Example 5

A nutritional composition for tonifying kidney includes the following components of raw materials in parts by weight: rice 70, yellow millet 15, gordon euryale seed 7, Chinese yam 6, *lycium barbarum* 1, and poria 1.

A preparation method is as follows:

step 1, preparing raw materials: purifying and sorting rice, yellow millet, gordon euryale seed, Chinese yam, *lycium barbarum*, and poria for subsequent use;

step 2, frying: frying respective components of raw materials under a condition of 150° C. for 40 min;

step 3, dosing: grinding the respective fried raw materials, then mixing and stirring evenly the respective ground raw materials according to proportions to obtain a rice powder;

step 4, granulating: extruding the rice powder obtained in step 3 through a double-screw extruder, followed by gelatinization and granulation, to obtain mixed rice grains, wherein temperatures of three phases of the double-screw extruder are kept at 60° C., 110° C., and 90° C., respectively;

step 5: drying: drying the mixed rice grains through a microwave dryer, wherein a water content of the material is kept below 12%, and cooling the dried mixed rice grains at a room temperature, wherein a heating temperature of the microwave dryer is kept at 55° C.;

step 6: sieving and packaging: sieving the cooled mixed rice grains, and vacuum-packaging the sieved mixed rice grains.

Example 6

A nutritional composition for tonifying kidney includes the following components of raw materials in parts by weight: rice 70, yellow millet 15, gordon euryale seed 7, Chinese yam 6, *lycium barbarum* 1, poria 1, and a Chinese herbal medicine extract 1. The Chinese herbal medicine extract includes the following components of raw materials in parts by weight: *perilla* 30, raspberry 28, cinnamon 28, fennel 20, and ginger 23. The Chinese herbal medicine extract is prepared through the following method: drying and grinding respective raw materials into a medicinal powder, subjecting the medicinal powder to ultrasonic extraction, centrifugation, and concentration with an ethanol solution of 65% in volume percentage to obtain the Chinese herbal medicine extract. In a process of preparing the Chinese herbal medicine extract, a vacuum dryer is used for drying, a temperature parameter is 75° C., and a vacuum degree is a negative pressure of 0.08 MPa.

A method for preparing the nutritional composition for tonifying kidney is as follows:

step 1, preparing raw materials: purifying and sorting rice, yellow millet, gordon euryale seed, Chinese yam, *lycium barbarum*, and poria for subsequent use;

step 2, frying: frying respective components of raw materials under a condition of 150° C. for 40 min;

step 3, dosing: grinding the respective fried raw materials, then mixing and stirring evenly the respective ground raw materials according to proportions to obtain a rice powder;

step 4, granulating: extruding the rice powder obtained in step 3 through a double-screw extruder, followed by gelatinization and granulation, to obtain mixed rice grains, wherein temperatures of three phases of the double-screw extruder are kept at 60° C., 110° C., and 90° C., respectively;

step 5: drying: drying the mixed rice grains through a microwave dryer, wherein a water content of the material is kept below 12%, and cooling the dried mixed rice grains at a room temperature, wherein a heating temperature of the microwave dryer is kept at 55° C.;

step 6: sieving and packaging: sieving the cooled mixed rice grains, and vacuum-packaging the sieved mixed rice grains.

Example 7

A nutritional composition for tonifying kidney includes the following components of raw materials in parts by weight: rice 70, yellow millet 15, gordon euryale seed 7, Chinese yam 6, *lycium barbarum* 1, poria 1, and a Chinese herbal medicine extract 1. The Chinese herbal medicine extract includes the following components of raw materials in parts by weight: *perilla* 15, raspberry 17, cinnamon 16, fennel 10, and ginger 16. The Chinese herbal medicine extract is prepared through the following method: drying and grinding respective raw materials into a medicinal powder, subjecting the medicinal powder to ultrasonic extraction, centrifugation, and concentration with an ethanol solution of 40% volume percentage to obtain the Chinese herbal medicine extract. In a process of preparing the Chinese herbal medicine extract, a vacuum dryer is used for drying, a temperature parameter is 80° C., and a vacuum degree is a negative pressure of 0.1 MPa.

A method for preparing the nutritional composition for tonifying kidney is as follows:

step 1, preparing raw materials: purifying and sorting rice, yellow millet, gordon euryale seed, Chinese yam, *lycium barbarum*, and poria for subsequent use;

step 2, frying: frying respective components of raw materials treated in step 1 under a condition of 150° C. for 40 min;

step 3, dosing: grinding the respective fried raw materials, then mixing and stirring evenly the respective ground raw materials with the Chinese herbal medicine extract according to proportions to obtain a rice powder;

step 4, granulating: extruding the rice powder obtained in step 3 through a double-screw extruder, followed by gelatinization and granulation, to obtain mixed rice grains, wherein temperatures of three phases of the double-screw extruder are kept at 60° C., 110° C., and 90° C., respectively;

step 5: drying: drying the mixed rice grains through a microwave dryer, wherein a water content of the material is kept below 12%, and cooling the dried mixed rice grains at a room temperature, wherein a heating temperature of the microwave dryer is kept at 55° C.;

step 6: sieving and packaging: sieving the cooled mixed rice grains, and vacuum-packaging the sieved mixed rice grains.

Experiment Example 1: Sensory Evaluation of Eating Quality

Evaluating method: scoring is made in comparison with reference samples according to the odor, appearance structure, palatability, taste, and cold rice texture of the rice, and an overall score is sum of respective items. Scoring rules are shown in Table 1. Products used for the sensory evaluation of this experiment example are staple foods, numbered as products 1 to 7, obtained by mixing the nutritional compositions for tonifying kidney obtained in Examples 1 to 7 of the present invention with rice, respectively, a mixing ratio of rice to the nutritional composition for tonifying kidney being 4:1. Statistical results of the evaluation scores corresponding to the products 1 to 7 are shown in Table 2.

An overall score of less than 50 indicates "very bad", 51-60 "bad", 61-70 "ordinary", 71-80 "relatively good", 81-90 "good", and more than 90 "excellent".

Uncovered matters such as specific operation steps, preparation work, evaluator determination, sample approval, instrument, and appliance should comply with GB/T 15682-2008 Inspection of Grain and Oils—Method for Sensory Evaluation of Paddy or Rice Cooking and Eating Quality.

TABLE 1

Scoring Rules for Sensory Evaluation of Steamed Rice

| First-grade Index Score | Second-grade Index Score | Description of specific properties: score |
|---|---|---|
| Odor 20 | Authenticity and Intensity 20 | Having unique aroma of steamed rice, rich in fragrance: 18~20 |
| | | Having unique aroma of steamed rice, delicate in fragrance of steamed rice: 15~17 |
| | | Having unique aroma of steamed rice, but not obvious in fragrance: 12~14 |
| | | Having no fragrance, but without undesirable odor: 7~12 |
| | | Having an undesirable odor: 0~6 |
| Appearance Structure 20 | Color 7 | Bright in color: 6~7 |
| | | Normal in color: 4~5 |
| | | Dull in color: 0~3 |
| | Gloss 8 | Having obvious gloss: 7~8 |
| | | Slightly glossy: 5~6 |
| | | Having no gloss: 0~4 |

TABLE 1-continued

Scoring Rules for Sensory Evaluation of Steamed Rice

| First-grade Index Score | Second-grade Index Score | Description of specific properties: score |
|---|---|---|
| Palatability 30 | Integrity of Steamed Rice Grain 5 | Compact steamed rice structure, good integrity of steamed rice grain: 4~5<br>Most of the steamed rice having a compact and complete structure: 3<br>Some steamed rice grains explode: 0~2 |
| | Viscosity 10 | Smooth, Viscous, not sticky to teeth: 8~10<br>Viscous, basically not sticky to teeth: 6~7<br>Viscous, sticky to teeth; or not viscous: 0~5 |
| | Elasticity 10 | Chewy: 8~10<br>Slightly shewy: 6~7<br>Loose, hard, feeling foreign matters present: 0~5 |
| | Hardness 10 | Neither too hard nor too soft: 8~10<br>Slightly hard or slightly soft: 6~7<br>Very hard or very soft: 0~5 |
| Taste 25 | Authenticity and Persistence 25 | Having relatively strong fragrance and sweet taste when chewed: 22~25<br>Having light fragrance and sweet taste when chewed: 18~21<br>Having no fragrance or sweet taste when chewed, but without undesirable odor: 16~17<br>Having no fragrance or sweet taste when chewed, but having an undesirable odor: 0~15 |
| Cold Steamed Rice Texture 5 | Agglomeration, Viscoelasticity, and Hardness 5 | Relatively loose, relatively good in viscoelasticity, moderate in hardness: 4~5<br>Agglomerated, slightly bad in viscoelasticity, slightly hardened: 2~3<br>Hardened, bad in viscoelasticity, and more rigid: 0~1 |

TABLE 2

Statistical Table of Results of Evaluation Scores of Respective Products

| Group | Overall Score/Score | Evaluation Result |
|---|---|---|
| Product 1 | 87 | Good |
| Product 2 | 90 | Excellent |
| Product 3 | 88 | Good |
| Product 4 | 95 | Excellent |
| Product 5 | 93 | Excellent |
| Product 6 | 91 | Excellent |
| Product 7 | 93 | Excellent |

It can be seen from the above test results that all the sensory evaluation results made by respective sensory evaluators on the nutritional compositions for tonifying kidney prepared in Examples 1 to 7 in conjunction with rice are "excellent" and "good". It is indicated that the products of the present invention have relatively excellent performances in odor, appearance structure, palatability, taste, and cold rice texture.

Experiment Example 2: Animal Experiment

By designing kidney-deficiency animal models, test and research of loaded swimming of kidney-deficiency model mice is conducted for the nutritional compositions obtained in Examples 1 to 7. Results show that Examples 1-7 of the present invention can significantly increase the low-temperature swimming time and times of locomotor activities of the kidney-deficiency mice, effects of which are obviously better than a kidney-deficiency model group, indicating that this nutritional composition has the anti-fatigue capability and has certain health-care curative effect to kidney deficiency.

The foregoing only describes preferred examples of the present invention and is not intended to limit the present invention. For a person skilled in the art, various modifications and variations may be made to the present invention. Any modifications, equivalent replacements, improvements, etc., made within the spirit and principle of the present invention, should be covered by the scope of protection of the present invention.

What is claimed is:

1. A method for preparing a nutritional composition for tonifying kidney, wherein the method comprises the following steps in sequence:
   step 1, preparing raw materials: purifying and sorting rice, yellow millet, gordon euryale seed, Chinese yam, *lycium barbarum*, and poria for subsequent use;
   step 2, frying: frying respective components of raw materials under a condition of 100-200° C. for 25-120 min;
   step 3, dosing: grinding the respective fried raw materials, then mixing and stirring evenly the respective ground raw materials according to proportions to obtain a rice powder;
   step 4, granulating: extruding the rice powder obtained in step 3 through a double-screw extruder, followed by gelatinization and granulation, to obtain mixed rice grains;
   step 5: drying: drying the mixed rice grains through a microwave dryer, wherein a water content of the material is kept below 12%, and cooling the dried mixed rice grains at a room temperature;
   step 6: sieving and packaging: sieving the cooled mixed rice grains, and vacuum-packaging the sieved mixed rice grains.

2. The method for preparing a nutritional composition for tonifying kidney of claim 1, wherein temperatures of three phases of the double-screw extruder are kept at 60° C., 90-120° C., and 90° C., respectively.

3. The method for preparing a nutritional composition for tonifying kidney of claim 1, wherein a heating temperature of the microwave dryer is kept at 50-60° C.

4. The method for preparing a nutritional composition for tonifying kidney of claim 1, wherein in a dosing process of the step 3, a Chinese herbal medicine extract of 1-3 parts is further added, and the Chinese herbal medicine extract comprises the following components of raw materials in parts by weight: *perilla* 15-30, raspberry 17-28, cinnamon 16-28, fennel 10-20, and ginger 16-23.

5. The method for preparing a nutritional composition for tonifying kidney of claim 4, wherein the Chinese herbal medicine extract is prepared through the following method:
   drying and grinding respective raw materials into a medicinal powder, subjecting the medicinal powder to ultrasonic extraction, centrifugation, and concentration with an ethanol solution of 40-65% in volume percentage to obtain the Chinese herbal medicine extract.

6. The method for preparing a nutritional composition for tonifying kidney of claim 5, wherein in a process of preparing the Chinese herbal medicine extract, a vacuum dryer is used for drying, a temperature parameter is 75° C.-80° C., and a vacuum degree is between a negative pressure of 0.08 MPa and a negative pressure of 0.1 MPa.

7. The method for preparing a nutritional composition for tonifying kidney of claim 1, wherein in the step 1, purifying and sorting rice 50-90, yellow millet 7-25, gordon euryale seed 3-14, Chinese yam 2-11, *lycium barbarum* 0.4-1.6, and poria 0.3-1.5 for subsequent use.

8. The method for preparing a nutritional composition for tonifying kidney of claim 1, wherein in the step 1, purifying and sorting rice 60-80, yellow millet 10-20, gordon euryale seed 5-9, Chinese yam 4-8, *lycium barbarum* 0.7-1.3, and poria 0.6-1.2 for subsequent use.

9. The method for preparing a nutritional composition for tonifying kidney of claim 1, wherein in the step 1, purifying and sorting rice 70, yellow millet 15, gordon euryale seed 7, Chinese yam 6, *lycium barbarum* 1, and poria 1 for subsequent use.

* * * * *